United States Patent
Kato et al.

(10) Patent No.: US 11,957,802 B2
(45) Date of Patent: Apr. 16, 2024

(54) FLUID STERILIZATION APPARATUS AND FLUID STERILIZATION SYSTEM

(71) Applicant: Toshiba Lighting & Technology Corporation, Yokosuka (JP)

(72) Inventors: Takeo Kato, Ehime-ken (JP); Atsushi Fujioka, Ehime-ken (JP); Naoto Sakurai, Ehime-ken (JP); Seiya Iida, Ehime-ken (JP); Takanori Ochi, Ehime-ken (JP); Yukinobu Nakagawa, Ehime-ken (JP)

(73) Assignee: Toshiba Lighting & Technology Corporation, Yokosuka (JP)

( * ) Notice: Subject to any disclaimer, the term of this patent is extended or adjusted under 35 U.S.C. 154(b) by 489 days.

(21) Appl. No.: 17/173,350

(22) Filed: Feb. 11, 2021

(65) Prior Publication Data

US 2021/0322593 A1    Oct. 21, 2021

(30) Foreign Application Priority Data

Apr. 17, 2020 (JP) .................. 2020-074026
Jan. 14, 2021 (JP) .................. 2021-003925

(51) Int. Cl.
*A61L 2/10*    (2006.01)
*A61L 2/26*    (2006.01)
*C02F 1/32*    (2023.01)

(52) U.S. Cl.
CPC ............. *A61L 2/10* (2013.01); *A61L 2/26* (2013.01); *C02F 1/325* (2013.01); *A61L 2202/11* (2013.01); *A61L 2202/14* (2013.01); *A61L 2202/20* (2013.01); *C02F 2201/32* (2013.01); *C02F 2209/02* (2013.01)

(58) Field of Classification Search
CPC .......... A61L 2/10; A61L 2/26; A61L 2202/11; A61L 2202/14; A61L 2202/20; C02F 1/325
See application file for complete search history.

(56) References Cited

U.S. PATENT DOCUMENTS

2020/0171184 A1* 6/2020 Tanaka ............. C02F 1/325

FOREIGN PATENT DOCUMENTS

JP    2018-118201 A    8/2018

* cited by examiner

*Primary Examiner* — Sean E Conley
(74) *Attorney, Agent, or Firm* — Banner & Witcoff, Ltd.

(57) ABSTRACT

A fluid sterilization apparatus according to an embodiment includes a tubular cover; a tubular portion provided inside the cover; a supply head provided at one end of the tubular portion; a discharge head provided at the other end of the tubular portion; at least one light-emitting element provided in at least one of the supply head and the discharge head and allowed to irradiate an inside of the tubular portion with ultraviolet rays; and a temperature control unit capable of controlling a temperature of a space between the cover and the tubular portion.

20 Claims, 4 Drawing Sheets

FLUID STERILIZATION APPARATUS AND FLUID STERILIZATION SYSTEM

CROSS-REFERENCE TO RELATED APPLICATIONS

This application is based upon and claims the benefit of priority from Japanese Patent Application No. 2020-074026, filed on Apr. 17, 2020, and No. 2021-003925, filed on Jan. 14, 2021; the entire contents of which are incorporated herein by reference.

FIELD

Embodiments described herein relate generally to a fluid sterilization apparatus and a fluid sterilization system.

BACKGROUND

There is a fluid sterilization apparatus that sterilizes a fluid such as water by irradiating the fluid with ultraviolet rays. For example, there is a proposed fluid sterilization apparatus including a tubular portion through which a fluid flows and a light source provided at an end of the tubular portion to irradiate the inside of the tubular portion with ultraviolet rays. A part of the ultraviolet rays emitted from the light source directly irradiates the fluid flowing inside the tubular portion. In addition, the ultraviolet rays emitted from the light source and incident on the inner surface of the tubular portion propagate while repeating reflection inside the tubular portion.

Here, a temperature of the fluid flowing inside the tubular portion may be lower than a temperature of an environment in which the fluid sterilization apparatus is provided. In general, there is air containing water vapor in the environment where the fluid sterilization apparatus is provided. For this reason, when a difference between the temperature of the fluid and the temperature of the environment becomes large, dew condensation may occur on an outer surface of the tubular portion. When dew condensation occurs on the outer surface of the tubular portion and water adheres to the tubular portion, there is concern that an optical characteristic of the tubular portion may change. When the optical characteristic of the tubular portion changes, there is concern that bactericidal effect of ultraviolet rays propagating while repeating reflection inside the tubular portion may decrease.

Therefore, there is a desire for developing a technology that can suppress occurrence of dew condensation on the outer surface of the tubular portion.

DETAILED DESCRIPTION

Figure 1:
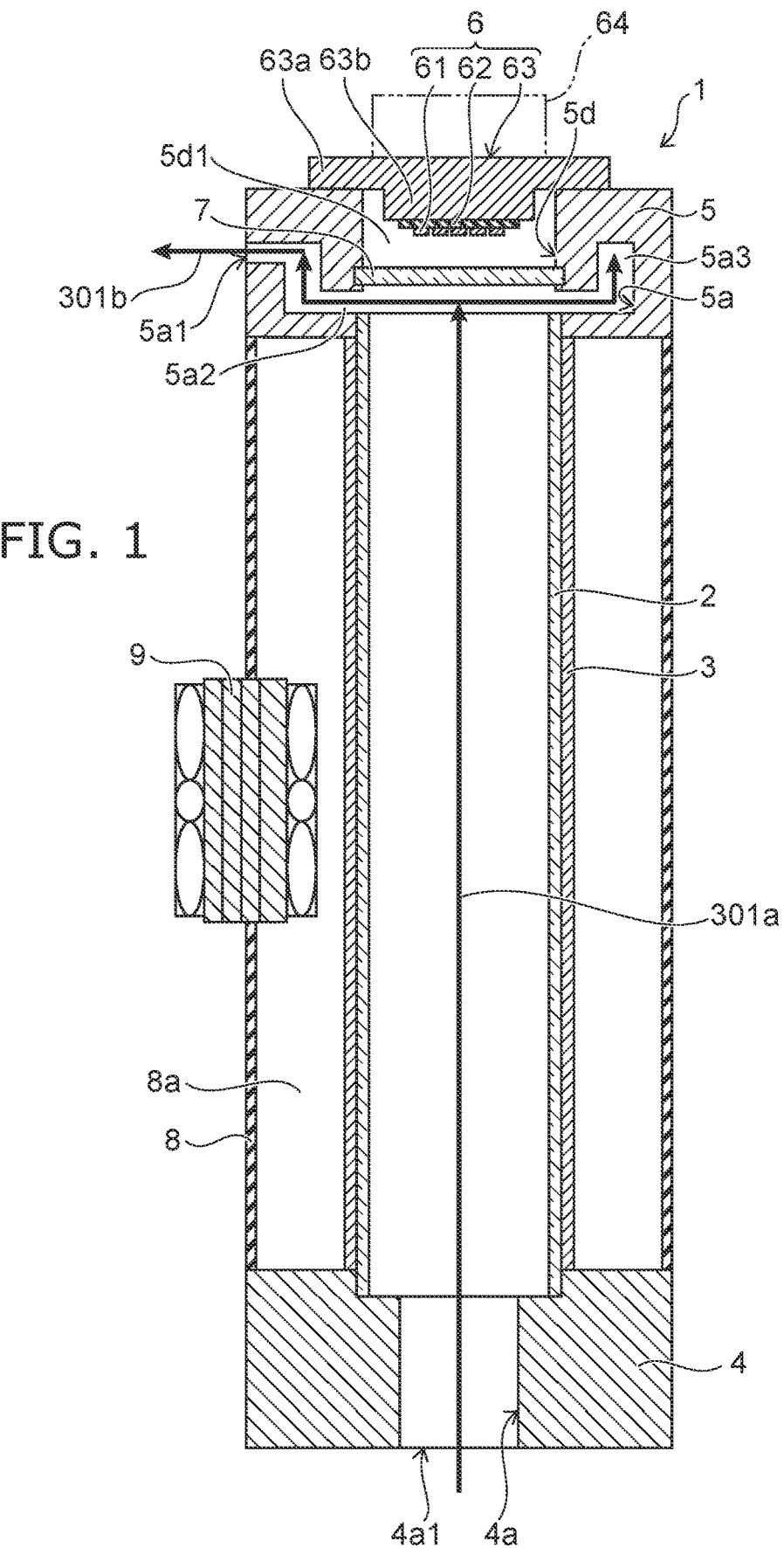
FIG. 1 is a schematic cross-sectional view for illustrating a fluid sterilization apparatus according to the present embodiment.

A fluid sterilization apparatus according to an embodiment includes a tubular cover; a tubular portion provided inside the cover; a supply head provided at one end of the tubular portion; a discharge head provided at the other end portion of the tubular portion; at least one light-emitting element provided in at least one of the supply head and the discharge head and allowed to irradiate the inside of the tubular portion with ultraviolet rays; and a temperature control unit capable of controlling a temperature of a space between the cover and the tubular portion.

Hereinafter, embodiments will be illustrated with reference to the drawings. Note that in each drawing, similar components are denoted by the same reference numerals and detailed description thereof will be omitted as appropriate.

(Fluid Sterilization Apparatus)

A fluid sterilization apparatus 1 according to the present embodiment can be used, for example, to sterilize a fluid having a temperature lower than an outside air temperature. For example, the fluid sterilization apparatus 1 can be used to sterilize well water, spring water, etc. during a high temperature period such as summer. However, the use of the fluid sterilization apparatus 1 is not limited to the examples.

FIG. 1 is a schematic cross-sectional view for illustrating the fluid sterilization apparatus 1 according to the present embodiment.

As illustrated in FIG. 1, the fluid sterilization apparatus 1 can be provided with a tubular portion 2, a reflective portion 3, a supply head 4, a discharge head 5, a light source 6, a window 7 (corresponding to an example of a first window), a cover 8, and a temperature control unit 9.

The tubular portion 2 has a tubular shape, and ends on both sides thereof are open. For example, the tubular portion 2 can be a cylindrical tube. A material of the tubular portion 2 is not particularly limited as long as the material is resistant to ultraviolet rays and a fluid 301a subjected to sterilization. For example, the material of the tubular portion 2 may be quartz or a fluororesin such as polytetrafluoroethylene (PTFE).

The reflective portion 3 can be provided on an outer surface of the tubular portion 2. The tubular portion 2 may be formed of a material that transmits ultraviolet rays, such as quartz. When a part of the ultraviolet rays emitted from the light source 6 passes through the tubular portion 2 and leaks to the outside, the processing capacity of the fluid sterilization apparatus 1 is lowered. When the reflective portion 3 is provided on the outer surface of the tubular portion 2, the ultraviolet rays directed to the outside of the tubular portion 2 can be reflected toward the inside of the tubular portion 2. For this reason, the utilization efficiency of the ultraviolet rays emitted from the light source 6 can be improved, and thus the number of light-emitting elements 61 can be reduced. When the number of light-emitting elements 61 is reduced, the size and cost of the light source 6 can be reduced.

The reflective portion 3 can be formed of a material having a high reflectance of ultraviolet rays. Examples of the material of the reflective portion 3 may include aluminum, an aluminum alloy, silicon dioxide, and polytetrafluoroethylene (PTFE). The reflective portion 3 has a plate shape and can be attached to the outer surface of the tubular portion 2. Further, the reflective portion 3 having a shape of a film can be formed on the outer surface of the tubular portion 2 using a film forming method such as a sputtering method or an evaporation method.

Further, even though a case where the reflective portion 3 is provided on the outer surface of the tubular portion 2 is illustrated, the reflective portion 3 may be provided on an inner side face of the tubular portion 2. However, when corrosion, etc. occurs due to contact between the reflective portion 3 and the fluid 301a (for example, water) before sterilization, or when the material of the reflective portion 3 melts out, the reflective portion is preferably formed on the outer surface of the tubular portion 2.

Further, the reflective portion 3 can be omitted. For example, when the tubular portion 2 is formed of a material that reflects ultraviolet rays (for example, a white inorganic material or a white resin), the reflective portion 3 can be omitted.

The supply head 4 is provided at one end of the tubular portion 2. A seal member such as an O-ring can be provided between the supply head 4 and the end of the tubular portion 2. The seal member is sealed so that a space between the supply head 4 and the tubular portion 2 is liquid-tight.

For example, the supply head 4 has a cylindrical shape and has a hole 4a penetrating between one end face and the other end face. One opening of the hole 4a is connected to the inside of the tubular portion 2. The other opening of the hole 4a serves as a supply port 4a1. A supply source of the fluid 301a can be connected to the supply port 4a1 via a pipe (see FIG. 4). Further, a filter, a current plate, etc. can be provided inside the hole 4a.

A material of the supply head 4 is not particularly limited as long as the material is resistant to the fluid 301a and ultraviolet rays. The material of the supply head 4 can be, for example, a metal such as stainless steel.

The discharge head 5 is provided at the other end of the tubular portion 2. A seal member such as an O-ring can be provided between the discharge head 5 and the end of the tubular portion 2. The seal member is sealed so that a space between the discharge head 5 and the tubular portion 2 is liquid-tight.

For example, the discharge head 5 has a cylindrical shape and has a hole 5a and a hole 5d. One opening of the hole 5a is connected to the inside of the tubular portion 2. The other opening of the hole 5a serves as a discharge port 5a1 provided on a side face of the discharge head 5. For example, a tank 105, etc. can be connected to the discharge port 5a1 via a pipe (see FIG. 4).

A material of the discharge head 5 is not particularly limited as long as the material is resistant to a fluid 301b after sterilization and ultraviolet rays. The material of the discharge head 5 can be, for example, a metal such as stainless steel.

As illustrated in FIG. 1, the hole 5a is a bent flow path. The hole 5a has a flow path 5a2 substantially parallel to an end face of the discharge head 5 on the tubular portion 2 side, and a flow path 5a3 extending in an axial direction of the discharge head 5.

The flow path 5a2 is open to the end face of the discharge head 5 on the tubular portion 2 side. Further, the window 7 is exposed on an inner wall of the flow path 5a2. The flow path 5a2 can be, for example, a disk-shaped space.

One end of the flow path 5a3 is connected to the vicinity of a peripheral edge of the flow path 5a2. The other end of the flow path 5a3 is connected to the discharge port 5a1. The flow path 5a3 can be, for example, a cylindrical space.

As illustrated in FIG. 1, the fluid 301a supplied to the inside of the tubular portion 2 via the supply head 4 is supplied to the inside of the flow path 5a2. The fluid 301a supplied to the inside of the flow path 5a2 hits the window 7 and flows along a surface of the window 7 toward a peripheral edge side of the window 7. In this instance, the fluid 301a is sterilized by ultraviolet rays emitted through the window 7. The sterilized fluid 301b is discharged from the discharge port 5a1 via the flow path 5a3.

Note that a part of ultraviolet rays emitted to the flow path 5a2 is emitted to the inside of the tubular portion 2. Further, a part of the ultraviolet rays emitted to the inside of the tubular portion 2 is reflected by the reflective portion 3. For this reason, the fluid 301a is sterilized in the inside of the tubular portion 2.

The hole 5d is open to the end face of the discharge head 5 on the opposite side to the tubular portion 2 side and the flow path 5a2.

For example, the light source 6 can be detachably provided in the discharge head 5.

The light source 6 has, for example, a light-emitting element 61, a board 62 (corresponding to an example of a first board or a second board), and a holder 63.

The light-emitting element 61 is provided on the board 62 and can irradiate the window 7 with ultraviolet rays. That is, the light-emitting element 61 can irradiate the inside of the tubular portion 2 with ultraviolet rays. At least one light-emitting element 61 can be provided. When a plurality of light-emitting elements 61 is provided, the plurality of light-emitting elements 61 can be connected in series. The light-emitting element 61 is not particularly limited as long as the light-emitting element 61 is an element that generates ultraviolet rays. The light-emitting element 61 can be, for example, an LED or a laser diode.

A peak wavelength of the ultraviolet rays emitted from the light-emitting element 61 is not particularly limited as long as the bactericidal effect is obtained. However, when the peak wavelength is 260 nm to 280 nm, the bactericidal effect can be improved. For this reason, it is preferable to that the light-emitting element 61 can emit ultraviolet rays having a peak wavelength of 260 nm to 280 nm.

The board 62 has a plate shape and is provided on a surface of the holder 63 on the window 7 side. A wiring pattern can be provided on one surface of the board 62. The light-emitting element 61 can be mounted on the writing pattern of the board 62. That is, at least one light-emitting element 61 is provided on the board 62. A material of the board 62 is preferably resistant to ultraviolet rays. The material of the board 62 can be, for example, ceramics such as aluminum oxide. The board 62 may be a metal plate whose surface is covered with an inorganic material (metal core board). When the material of the board 62 is ceramics, etc., or when the board 62 is a metal core board, it is possible to obtain resistance to ultraviolet rays and a high thermal radiation property.

The holder 63 can be detachably provided on the discharge head 5. The light-emitting element 61 has a longer life than that of a discharge lamp, etc. However, the light-emitting efficiency decreases as the lighting time becomes longer. Further, it is also conceivable that the light-emitting element 61 may break down or a defect may occur in the writing pattern of the board 62. When the holder 63 is detachably provided on the discharge head 5, the light-emitting element 61 and the board 62 can be easily removed together with the holder 63, so that maintenance work becomes easy.

The holder 63 may include, for example, a flange 63a and a convex portion 63b. The flange 63a and the convex portion 63b can be integrally formed.

The flange 63a has a plate shape and can be attached to the end face of the discharge head 5 on the opposite side to the tubular portion 2 side. The flange 63a can be attached to the discharge head 5 using, for example, a fastening member such as a screw.

The convex portion 63b is provided on a surface of the flange 63a on the tubular portion 2 side. The board 62 on which the light-emitting element 61 is mounted can be provided on an end face of the convex portion 63b on the tubular portion 2 side. Further, the convex portion 63b may have a function of determining a position of the light-emitting element 61 with respect to the discharge head 5. For example, a side face of the convex portion 63b can be brought into contact with an inner wall of the hole 5d of the discharge head 5. In this way, it is possible to determine the position of the light-emitting element 61 with respect to the discharge head 5.

Further, since the hole 5d of the discharge head 5 and the flow path 5a2 are separated by the window 7, the light source 6 (holder 63) can be attached and detached even when the fluid 301a is present in the flow path 5a2.

Further, the holder 63 can have a function of releasing heat generated in the light-emitting element 61 to the outside. For this reason, the holder 63 is preferably formed of a material having high thermal conductivity. The holder 63 can be formed of, for example, a metal such as aluminum, copper, or stainless steel.

Further, thermal radiation fins, a cooling apparatus 64, etc. can be provided on an end face, etc. of the holder 63 on the opposite side from the light-emitting element 61 side. The cooling apparatus 64 can be, for example, a fan that supplies air to the holder 63. Further, when the holder 63 is provided with the thermal radiation fins, the cooling apparatus 64 may be fans that supply air to the thermal radiation fins. Further, for example, the cooling apparatus 64 may supply a refrigerant to a flow path provided in the holder 63. That is, the cooling apparatus 64 may be of an air-cooled type or a liquid-cooled type.

Note that the cooling apparatus 64 can be omitted depending on the number or the heat generation amount of light-emitting elements 61, the temperature or the flow rate of the fluid 301a, etc. However, if the cooling apparatus 64 is provided, even when the number of light-emitting elements 61 and the applied power are increased, the temperature of the light-emitting element 61 hardly exceeds a maximum junction temperature.

The window 7 has a plate shape and is provided on the inner wall of the hole 5d of the discharge head 5 so as to be liquid-tight. That is, the window 7 is provided on the discharge head 5, and one surface of the window 7 is exposed to the flow path 5a2 provided in the discharge head 5. A space 5d1 can be provided between the window 7 and the board 62. The window 7 can be formed of a material that is capable of transmitting ultraviolet rays and has resistance to ultraviolet rays and the fluid 301a. The window 7 can be formed of, for example, quartz, a fluororesin that transmits ultraviolet rays, etc.

Further, an antireflection film may be provided on a surface of the window 7 on the light-emitting element 61 side. When the antireflection film is provided, it is possible to prevent the ultraviolet rays emitted from the light-emitting element 61 from being reflected by the window 7 and becoming difficult to irradiate the fluid 301a. That is, it is possible to improve the utilization efficiency of the ultraviolet rays emitted from the light-emitting element 61.

Further, an antifouling film can be provided on the surface of the window 7 on the tubular portion 2 side. The fluid 301a may contain impurities. When impurities adhere to the window 7, it becomes difficult for the ultraviolet rays emitted from the light-emitting element 61 to pass through the window 7. When the antifouling film is provided, it is possible to inhibit the impurities from adhering to the window 7. For this reason, it is possible to suppress the difficulty in irradiating the fluid 301a with ultraviolet rays over time.

The cover 8 has a tubular shape, and the tubular portion 2 and the reflective portion 3 can be accommodated therein. A space 8a is provided between the cover 8 and the outer surface of the reflective portion 3 (tubular portion 2). The cover 8 can be attached to, for example, the supply head 4 and the discharge head 5. A method of attaching the cover 8 is not particularly limited. For example, one end of the cover 8 can be provided inside a groove provided in the supply head 4, and the other end of the cover 8 can be provided inside a groove provided in the discharge head 5. Further, for example, flanges may be provided at the ends of the cover 8 on both sides, so that one flange may be attached to the supply head 4 using a screw, etc., and the other flange may be attached to the discharge head 5 using a screw, etc.

Here, the temperature of the fluid 301a flowing inside the tubular portion 2 may be lower than the temperature of the environment in which the fluid sterilization apparatus 1 is provided. For example, groundwater, spring water, etc. may be sterilized during a high temperature period such as summer. The space 8a between the cover 8 and the outer surface of the reflective portion 3 (tubular portion 2) contains a gas such as air. In general, the gas contained in the space 8a becomes air in an environment in which the cover 8 is attached to the supply head 4 and the discharge head 5. For this reason, air containing water vapor is present in the space 8a.

In this case, when the difference between the temperature of the fluid 301a and the temperature of the environment in which the fluid sterilization apparatus 1 is provided becomes large, the water vapor contained in the space 8a may be condensed to cause dew condensation on the outer surface of the reflective portion 3 (tubular portion 2).

The ultraviolet rays emitted from the light source 6 and incident on the inner surface of the tubular portion 2 propagate while repeating reflection inside the tubular portion 2. When water generated by dew condensation adheres to the outer surface of the tubular portion 2 or enters between the outer surface of the tubular portion 2 and the reflective portion 3, an optical characteristic of the reflective portion 3 or the tubular portion 2 (for example, reflectance, etc.) may change. The ultraviolet rays that propagate while being repeatedly reflected inside the tubular portion 2 contribute to sterilization. Therefore, when the optical characteristic of the reflective portion 3, etc. changes, there is concern that the bactericidal effect may decrease.

Therefore, the fluid sterilization apparatus 1 according to the present embodiment is provided with the temperature control unit 9.

The temperature control unit 9 may be provided on the cover 8. The temperature control unit 9 can control the temperature of the space 8a between the cover 8 and the reflective portion 3 (tubular portion 2). For example, the temperature control unit 9 reduces a difference between the temperature of the gas contained in the space 8a and the temperature of the fluid 301a supplied to the inside of the tubular portion 2. The temperature control unit 9 may be, for example, a Peltier element. When the temperature control unit 9 is the Peltier element, the gas contained in the space 8a can be cooled or the gas contained in the space 8a can be heated by changing a direction of a current flowing through the Peltier element. The Peltier element is a plate-shaped element, and thus can be easily provided on the outer surface or the inner surface of the cover 8. Further, as illustrated in FIG. 1, a hole may be provided in the cover 8 and the temperature control unit 9 may be provided inside the hole.

Note that the temperature control unit 9 may include a flow path for circulating a heat medium. For example, the temperature control unit 9 may be a water-cooled jacket, etc. Further, the temperature control unit 9 may include a blower, a heater, etc. However, when the temperature control unit 9 is the Peltier element, the temperature control unit 9 can be downsized, and the fluid sterilization apparatus 1 can be downsized. Further, by changing the direction of the flowing current, the gas contained in the space 8a can be cooled or the gas contained in the space 8a can be heated, so that the temperature can be easily controlled.

Further, in consideration of suppressing dew condensation, it is preferable to provide a seal member such as a packing or an O-ring between the cover 8 and the supply head 4. It is preferable to provide a seal member such as a packing or an O-ring between the cover 8 and the discharge head 5. When the seal member is provided, it is possible to prevent air, etc. containing a large amount of external water vapor from entering the space 8a.

Further, in consideration of suppressing dew condensation, it is preferable that the amount of water vapor contained in the space 8a is small. For example, it is preferable that the relative humidity in the space 8a is 80% or less. For example, in an environment where the relative humidity is 80% or less, the cover 8 may be attached to the supply head 4 and the discharge head 5. Further, a dehumidifying agent, etc. can be provided in the space 8a.

Further, in consideration of suppressing dew condensation, a material of the cover 8 is preferably a material having a low thermal conductivity. For example, the cover 8 may be formed of, for example, a resin such as a phenol resin or a fluororesin, an inorganic material such as ceramics, etc. Further, a material having a high thermal conductivity such as a metal and a material having a low thermal conductivity such as a resin may be superposed. Further, a heat insulating material may be provided on at least one of the outer surface and the inner surface of the cover 8. In this way, it is possible to suppress propagation of heat between the outside air and the gas contained in the space 8a, so that temperature control by the temperature control unit 9 can be facilitated.

Figure 2:
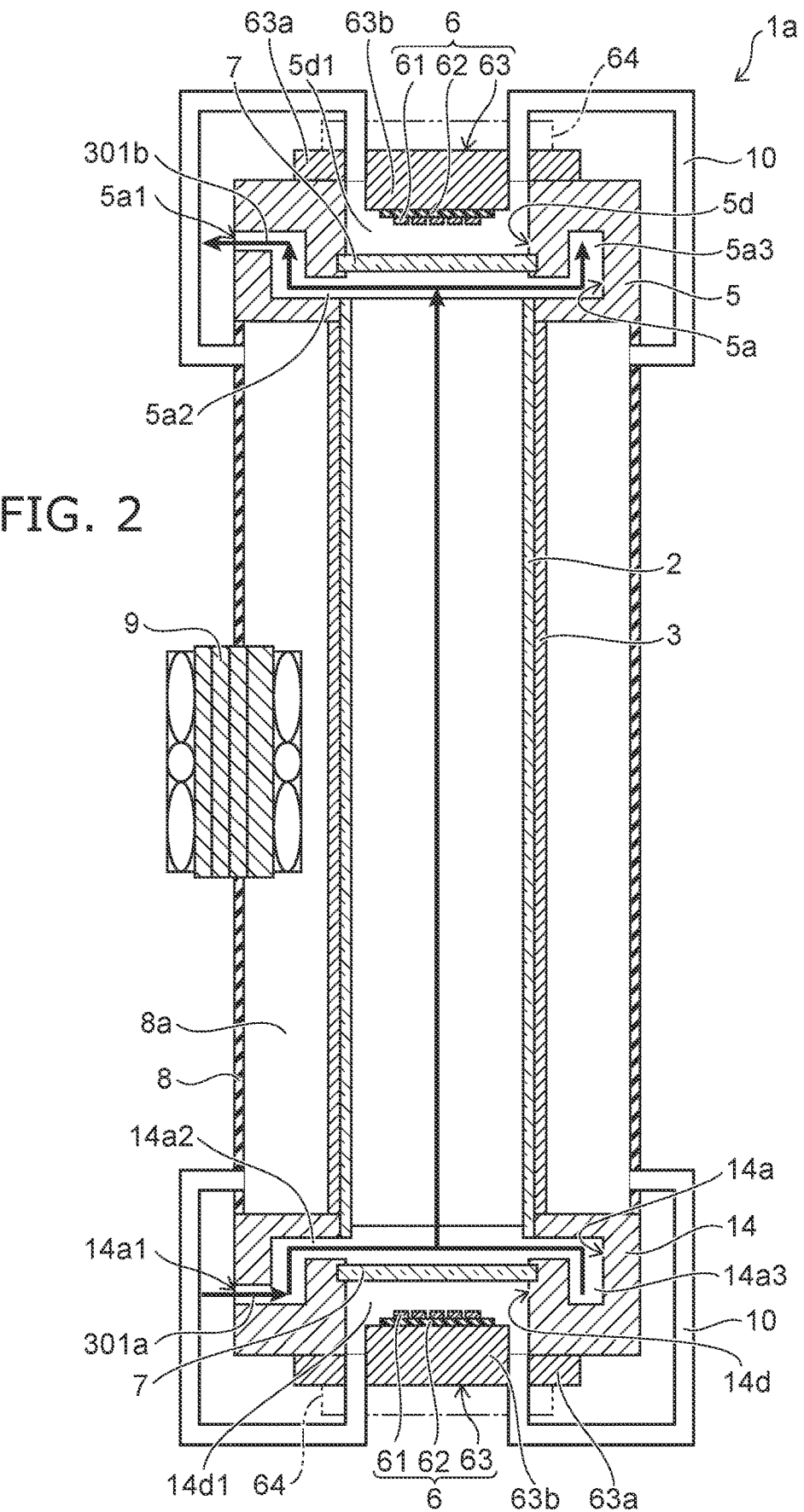
FIG. 2 is a schematic cross-sectional view for illustrating a fluid sterilization apparatus according to another embodiment.

FIG. 2 is a schematic cross-sectional view for illustrating a fluid sterilization apparatus 1a according to another embodiment.

As illustrated in FIG. 2, the fluid sterilization apparatus 1a may be provided with a tubular portion 2, a reflective portion 3, a supply head 14, a discharge head 5, a light source 6, a window 7, a cover 8, a temperature control unit 9, and a communication portion 10 (corresponding to an example of a first communication portion or a second communication portion).

In the case of the fluid sterilization apparatus 1 illustrated in FIG. 1, the discharge head 5 is provided with the light source 6 (light-emitting element 61), and the supply head 4 is not provided with the light source 6 (light-emitting element 61). Note that the supply head 4 may be provided with the light source 6 (light-emitting element 61), and the discharge head 5 may not be provided with the light source 6 (light-emitting element 61). In the case of the fluid sterilization apparatus 1a according to the present embodiment, a light source 6 (light-emitting element 61) is provided in each of the supply head 14 and the discharge head 5. That is, the light source 6 (light-emitting element 61) may be provided in at least one of the supply head and the discharge head. In this case, when the light source 6 (light-emitting element 61) is provided in each of the supply head and the discharge head, the amount of the fluid 301a for sterilization can be increased, or a length of the tubular portion 2 in a central axis direction can be increased. Further, when a plurality of light-emitting elements 61 having a large amount of heat generation is provided, the plurality of light-emitting elements 61 may be separately provided as the light source 6 on the supply head side and the light source 6 on the discharge head side. For this reason, even in the light-emitting element 61 having a large amount of heat generation, it is possible to inhibit the temperature of the light-emitting element 61 from exceeding the maximum junction temperature.

Note that when the light source 6 is provided in the supply head, the window 7 (corresponding to an example of a second window) may be provided in the supply head. That is, the window 7 is provided in the supply head 14, and one surface is exposed to a flow path 14a2 provided in the supply head 14.

As illustrated in FIG. 2, for example, the supply head 14 provided with the light source 6 and the window 7 may have the same configuration as that of the discharge head 5. For example, a material of the supply head 14 may be the same as a material of the discharge head 5.

For example, holes 14a and 14d provided in the supply head 14 may be the same as holes 5a and 5d provided in the discharge head 5. In this case, one opening of the hole 14a is connected to the inside of the tubular portion 2. The other opening of the hole 14a serves as a supply port 14a1 provided on a side face of the supply head 14. For example, a water source, etc. can be connected to the supply port 14a1 via a pipe. Further, a filter, a current plate, etc. may be provided inside the supply port 14a1.

Further, the flow path 14a2 and a flow path 14a3 provided in the hole 14a may be the same as a flow path 5a2 and a flow path 5a3 provided in the hole 5a. For example, the flow path 14a2 is open to an end face of the supply head 14 on the tubular portion 2 side. Further, the window 7 is exposed on an inner wall of the flow path 14a2. One end of the flow path 14a3 is connected to the vicinity of a peripheral edge of the flow path 14a2. The supply port 14a1 is connected to the other end of the flow path 14a3.

As illustrated in FIG. 2, the fluid 301a supplied to the inside of the flow path 14a2 through the supply port 14a1 and the flow path 14a3 flows to a center side of the window 7 along a surface of the window 7. At this time, the fluid 301a is sterilized by ultraviolet rays emitted through the window 7. Further, the fluid 301a flows inside the tubular portion 2 toward the discharge head 5 side and is supplied to the inside of the flow path 5a2 of the discharge head 5. The fluid 301a supplied to the inside of the flow path 5a2 hits the window 7 and flows along a surface of the window 7 toward the peripheral edge side of the window 7. At this time, the fluid 301a is sterilized by ultraviolet rays emitted through the window 7. The sterilized fluid 301b is discharged from the discharge port 5a1 via the flow path 5a3.

When the holes 14a and 5a are bent in this way, the flow velocity of the fluid 301a flowing inside the flow paths 14a2 and 5a2 can be slowed down. For this reason, the residence time of the fluid 301a in a region where the window 7 is exposed can be lengthened, so that the bactericidal effect can be improved.

Note that a part of the ultraviolet rays emitted to the flow path 14a2 and the flow path 5a2 is emitted to the inside of the tubular portion 2. Further, a part of the ultraviolet rays emitted to the inside of the tubular portion 2 is reflected by the reflective portion 3. For this reason, the fluid 301a is sterilized inside the tubular portion 2.

The communication portion 10 communicates with a space 5d1 (space 14d1) between a surface of the window 7 on the light-emitting element 61 side and the board 62 and a space 8a between the cover 8 and the reflective portion 3 (tubular portion 2). For example, communication portion 10 may have a shape of a pipe. One end of the communication portion 10 can be connected to the space 8a through a hole provided on the outer surface of the cover 8. The other end of the communication portion 10 can be connected to the space 5d1 (space 14d1) through a hole provided in the holder 63.

When the communication portion 10 is provided, the space 8a and the space 5d1 (space 14d1) can be connected. When the communication portion 10 is provided, gas circulation can be generated between the space 8a and the space 5d1 (space 14d1). In this way, it is possible to suppress occurrence of dew condensation on the window 7. For this reason, it is possible to suppress the change in the optical characteristic of the surface of the window 7, and therefore it is possible to suppress the decrease in the bactericidal effect. Since the light-emitting element 61 is exposed inside the space 5d1 (space 14d1), when a gas flow occurs inside the space 5d1 (space 14d1), the light-emitting element 61 can be cooled. For this reason, it is possible to inhibit the temperature of the light-emitting element 61 from exceeding the maximum junction temperature.

Note that the number, arrangement, cross-sectional dimensions (inner diameter), etc. of communication portions 10 can be appropriately changed according to the number of light-emitting elements 61, the amount of heat generated, etc. The number, arrangement, cross-sectional dimensions (inner diameter), etc. of the communication portions 10 may be appropriately determined by conducting an experiment or a simulation.

Figure 3:
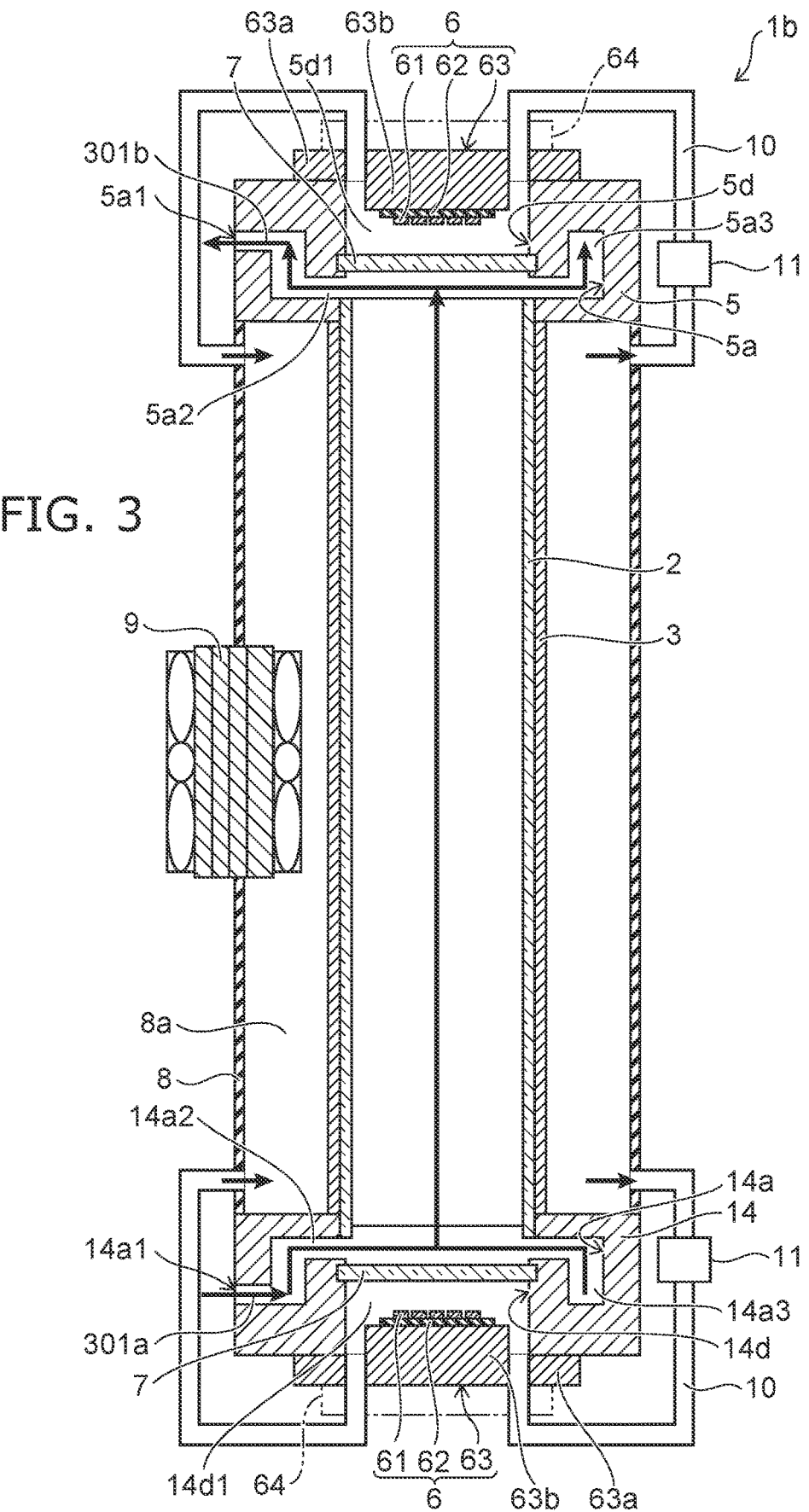
FIG. 3 is a schematic cross-sectional view for illustrating a fluid sterilization apparatus according to another embodiment.

FIG. 3 is a schematic cross-sectional view for illustrating a fluid sterilization apparatus 1b according to another embodiment.

As illustrated in FIG. 3, the fluid sterilization apparatus 1b may be provided with a tubular portion 2, a reflective portion 3, a supply head 14, a discharge head 5, a light source 6, a window 7, a cover 8, a temperature control unit 9, a communication portion 10, and a blower portion 11 (corresponding to an example of a first blower or a second blower).

The blower portion 11 generates a gas flow between a space 5d1 (space 14d1) between a surface of the window 7 on a light-emitting element 61 side and a board 62, and a space 8a between the cover 8 and the reflective portion 3 (tubular portion 2). For example, the blower portion 11 may be provided in the communication portion 10. For example, the blower portion 11 may be an air blower such as a pump or a blower. When the blower portion 11 is provided, gas circulation can be forcibly generated between the space 8a and the space 5d1 (space 14d1). For this reason, it is possible to effectively suppress occurrence of dew condensation on the window 7. Further, the light-emitting element 61 can be effectively cooled.

Note that when a plurality of communication portions 10 is provided, the blower portion 11 can be provided in at least one communication portion 10. In this case, it is preferable to allow a gas flow to be generated inside the space 5d1 and the space 14d1. For this reason, as illustrated in FIG. 3, it is preferable to provide the blower portion 11 in the communication portion 10 connected to the supply head 14 and to provide the blower portion 11 in the communication portion 10 connected to the discharge head 5.

(Fluid Sterilization System 100)

Figure 4:
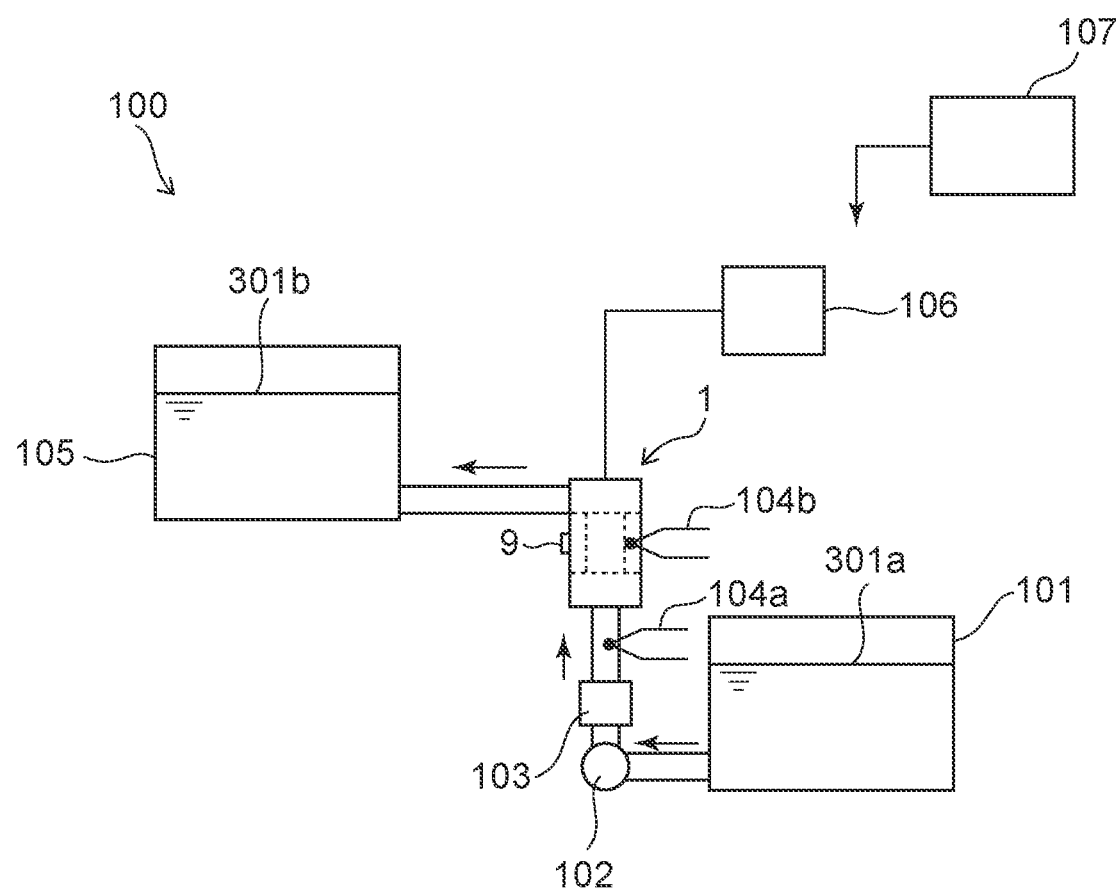
FIG. 4 is a schematic view for illustrating a fluid sterilization system according to the present embodiment.

FIG. 4 is a schematic view for illustrating a fluid sterilization system 100 according to the present embodiment. Note that even though a case where the fluid sterilization apparatus 1 is provided will be described as an example below, the description can be similarly applied to a case where the fluid sterilization apparatus 1a or 1b is provided.

As illustrated in FIG. 4, the fluid sterilization system 100 can include the fluid sterilization apparatus 1, a tank 101, a pump 102, a flow rate control valve 103, a temperature sensor 104a, a temperature sensor 104b, a tank 105, a power supply 106, and a controller 107.

The tank 101 can store the fluid 301a before sterilization. A discharge port of the tank 101 and the supply port 4a1 of the fluid sterilization apparatus 1 can be connected via, for example, a pipe.

The pump 102 can be provided in a pipe between the tank 101 and the fluid sterilization apparatus 1. The pump 102 supplies the fluid 301a stored in the tank 101 to the fluid sterilization apparatus 1. Note that for example, when the pump 102 pumps groundwater, spring water, etc., the tank 101 can be omitted. For example, when the fluid sterilization apparatus 1 is connected to a factory pipe, the tank 101 may be omitted, or the tank 101 and the pump 102 may be omitted.

The flow rate control valve 103 may be provided in a pipe between the pump 102 and the fluid sterilization apparatus 1. The flow rate control valve 103 controls a flow rate of the fluid 301a supplied to the fluid sterilization apparatus 1. Further, the flow rate control valve 103 can start and stop the supply of the fluid 301a.

Further, a filter, etc. can be appropriately provided in the supply head 4 of the fluid sterilization apparatus 1 or a pipe connected to the supply port 4a1.

The temperature sensor 104a detects the temperature of the fluid 301a supplied to the fluid sterilization apparatus 1. The temperature sensor 104b detects the temperature of the gas in the space 8a. The temperature sensors 104a and 104b may be, for example, a thermocouple, etc.

The tank 105 can be connected to the discharge port 5a1 of the fluid sterilization apparatus 1 via a pipe. The tank 105 can store the fluid 301b after sterilization (for example, water). Note that even though a case where the fluid 301b after sterilization is stored in the tank 105 is illustrated, the discharge port 5a1 of the fluid sterilization apparatus 1 may be connected to a device such as a cleaning device that uses the fluid 301b. Further, the fluid 301b discharged from the discharge port 5a1 of the fluid sterilization apparatus 1 may be flushed to an object such as a board.

The power supply 106 is electrically connected to the light source 6 (light-emitting element 61) of the fluid sterilization apparatus 1. The power supply 106 supplies predetermined electric power to the light source 6 (light-emitting element 61). The power supply 106 can be, for example, a DC power supply. The DC power supply may be provided with a rectifying circuit, a converter, a switch, etc. The rectifying circuit is electrically connected to an AC power supply. For example, the rectifying circuit can full-wave rectify an AC voltage applied by the AC power supply. For example, the rectifying circuit may include a diode bridge, etc. The converter converts the voltage full-wave rectified by the rectifying circuit into a predetermined DC voltage. For example, the converter may include a switching circuit. The switch can switch between applying electric power to the light source 6 (light-emitting element 61) and stopping the application of electric power.

For example, the controller 107 may include an arithmetic element such as a central processing unit (CPU) and a storage element such as a semiconductor memory. The controller 107 can be, for example, a computer. The storage element can store a control program that controls an operation of each element provided in the fluid sterilization system 100. The arithmetic element controls the operation of each element provided in the fluid sterilization system 100 using the control program stored in the storage element, data input by an operator, etc.

The controller 107 can control the temperature control unit 9 so that a difference between the temperature of the space 8a between the cover 8 and the reflective portion 3 (tubular portion 2) provided in the fluid sterilization apparatus 1 and the temperature of the fluid 301a supplied to the fluid sterilization apparatus 1 becomes small. For example, the controller 107 controls the temperature control unit 9 so that a difference between the temperature of the fluid 301a detected by the temperature sensor 104a and the temperature of the gas in the space 8a detected by the temperature sensor 104b becomes small. For example, in the case of sterilizing well water, etc. during a high temperature period such as summer, the temperature control unit 9 can cool the gas in the space 8a. In this way, it is possible to prevent the water vapor contained in the space 8a from condensing and causing dew condensation on the outer surface of the reflective portion 3 (tubular portion 2). For this reason, it is possible to suppress the change in the optical characteristic of the reflective portion 3, etc., and therefore it is possible to suppress the decrease in the bactericidal effect.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions. Moreover, above-mentioned embodiments can be combined mutually and can be carried out.

What is claimed is:

1. A fluid sterilization apparatus comprising:
a tubular cover;
a tubular portion provided inside the cover;
a supply head provided at one end of the tubular portion;
a discharge head provided at the other end of the tubular portion;
at least one light-emitting element provided in at least one of the supply head and the discharge head and allowed to irradiate an inside of the tubular portion with ultraviolet rays; and
a temperature control unit capable of controlling a temperature of a space between the cover and the tubular portion.

2. The apparatus according to claim 1, further comprising:
a first window provided in the discharge head, one surface thereof being exposed to a flow path provided in the discharge head;
a first board on which the light-emitting element is provided; and
at least one first communication portion communicating with a space between the other surface of the first window and the first board and a space between the cover and the tubular portion.

3. The apparatus according to claim 2, further comprising:
a first blower portion that generates a gas flow between the space between the other surface of the first window and the first board and the space between the cover and the tubular portion.

4. The apparatus according to claim 1, further comprising:
a second window provided in the supply head, one surface thereof being exposed to a flow path provided in the supply head;
a second board on which the light-emitting element is provided; and
at least one second communication portion communicating with a space between the other surface of the second window and the second board and the space between the cover and the tubular portion.

5. The apparatus according to claim 4, further comprising:
a second blower portion that generates a gas flow between a space between the other surface of the second window and the second board and a space between the cover and the tubular portion.

6. The apparatus according to claim 1, wherein the temperature control unit is provided on the cover.

7. The apparatus according to claim 1, wherein the temperature control unit is provided inside a hole provided in the cover.

8. The apparatus according to claim 1, wherein the temperature control unit is a Peltier element.

9. The apparatus according to claim 1, wherein the temperature control unit has a flow path for circulating a heat medium.

10. The apparatus according to claim 1, wherein the temperature control unit is a water-cooled jacket.

11. The apparatus according to claim 1, wherein the temperature control unit includes at least one of an air blower and a heater.

12. The apparatus according to claim 1, wherein a relative humidity in the space between the cover and the tubular portion is 80% or less.

13. The apparatus according to claim 1, wherein the cover contains at least one of a resin and an inorganic material.

14. The apparatus according to claim 13,
wherein the resin is a phenol resin or a fluororesin, and the inorganic material is ceramics.

15. The apparatus according to claim 2,
wherein the first communication portion has a shape of a pipe,
one end of the first communication portion is connected to the space between the cover and the tubular portion, and
the other end of the first communication portion is connected to the space between the other surface of the first window and the first board.

16. The apparatus according to claim 4,
wherein the second communication portion has a shape of a pipe,
one end of the second communication portion is connected to the space between the cover and the tubular portion, and
the other end of the second communication portion is connected to the space between the other surface of the second window and the second board.

17. The apparatus according to claim 3, wherein the first blower portion is provided in the first communication portion.

18. The apparatus according to claim 5, wherein the second blower portion is provided in the first communication portion.

19. A fluid sterilization system comprising:
the fluid sterilization apparatus according to claim 1; and
a controller capable of controlling a temperature control unit provided in the fluid sterilization apparatus,
the controller controlling the temperature control unit so that a difference between a temperature of a space between a cover and a tubular portion provided in the fluid sterilization apparatus and a temperature of a liquid supplied to the fluid sterilization apparatus becomes small.

20. The system according to claim 19, wherein the temperature of the liquid is lower than a temperature of an environment in which the fluid sterilization apparatus is provided.

* * * * *